(12) United States Patent
Loozen et al.

(10) Patent No.: US 6,677,329 B1
(45) Date of Patent: Jan. 13, 2004

(54) NON-AROMATIC ESTROGENIC STEROIDS WITH A HYDROCARBON SUBSTITUENT IN POSITION 11

(75) Inventors: Hubert Jan Jozef Loozen, Uden (NL); Gerrit Herman Veeneman, Schaijk (NL); Wilhelmus Gerardus Eduardus Joseph Schoonen, Oss (NL)

(73) Assignee: Akzo Nobel N V., Arnhem (NL)

( * ) Notice: Subject to any disclaimer, the term of this patent is extended or adjusted under 35 U.S.C. 154(b) by 23 days.

(21) Appl. No.: 10/070,262

(22) PCT Filed: Aug. 28, 2000

(86) PCT No.: PCT/EP00/08406

§ 371 (c)(1),
(2), (4) Date: May 29, 2002

(87) PCT Pub. No.: WO01/18027

PCT Pub. Date: Mar. 15, 2001

(30) Foreign Application Priority Data

Sep. 6, 1999 (EP) .............................. 99202900

(51) Int. Cl.$^7$ .............................. A61K 31/56; C07J 1/00
(52) U.S. Cl. .................... 514/182; 552/642; 552/644; 552/645; 552/649
(58) Field of Search .................. 514/182; 552/642, 552/644, 645, 649

(56) References Cited

U.S. PATENT DOCUMENTS

| | | |
|---|---|---|
| 3,092,645 A | 6/1963 | Nicholson |
| 3,377,366 A | 4/1968 | Baran |
| 3,464,979 A | 9/1969 | Barton |
| 3,465,010 A | 9/1969 | Baran |
| 3,652,606 A | 3/1972 | Baran |

FOREIGN PATENT DOCUMENTS

| | | |
|---|---|---|
| EP | 0 145 493 | 6/1985 |
| EP | 0 613 687 | 9/1994 |
| WO | 94 18224 | 8/1994 |
| WO | 99 45886 | 9/1999 |

OTHER PUBLICATIONS

Madden et al., "Metabolism of the contraceptive steroid desogestrel by human liver in vito." J. Steroid Biochem., vol. 15(2) pp. 281–288, 1990.*

* cited by examiner

*Primary Examiner*—Barbara P. Badio
(74) *Attorney, Agent, or Firm*—Mark W. Milstead

(57) ABSTRACT

Disclosed are novel, selective estrogens type having a steroid skeleton with a non-aromatic A-ring and a free or capped hydroxyl group at carbon atom No. 3. The estrogens satisfy general formula (I), in which $R^1$ is H, $(C_1-C_3)$alkyl or $(C_2-C_3)$acyl; $R^2$ is H, α-$(C_1-C_4)$alkyl, α-$(C_2-C_4)$alkenyl or α-$(C_2-C_4)$alkynyl; $R^3$ is H or $(C_1-C_4)$alkyl, $(C_2-C_4)$alkenyl or $(C_2-C_4)$alkynyl, each at location 15 or 16 of the steroid skeleton; $R^4$ is H or $(C_1-C_5)$alkyl, $(C_2-C_5)$alkenyl or $(C_2-C_5)$alkynyl, each optionally substituted with halogen; preferred is ethynyl; $R^5$ is H, $(C_1-C_3)$alkyl or $(C_2-C_3)$acyl; $R^6$ is $(C_1-C_5)$alkyl, $(C_2-C_5)$alkenyl, $(C_2-C_5)$alkynyl or $(C_1-C_5)$alkylidene, each optionally substituted.

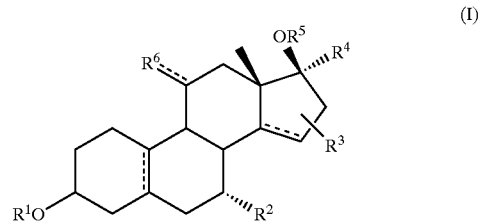

(I)

9 Claims, No Drawings

NON-AROMATIC ESTROGENIC STEROIDS WITH A HYDROCARBON SUBSTITUENT IN POSITION 11

This application is a 371 of PCT/EP00/08406 filed Aug. 28, 2000.

FIELD OF THE INVENTION

The invention is in the field of estrogenic compounds with a steroid skeleton having a non-aromatic A-ring and a free or capped hydroxyl group at carbon atom No. 3. Estrogenic compounds have a generally recognised utility in contraception and in the treatment of estrogen-deficiency related disorders, such as menopausal complaints, and osteoporosis.

BACKGROUND OF THE INVENTION

Many estrogenic compounds are known. For example, an instructive publication on estrogenic compounds with a non-aromatic A-ring and a free or capped hydroxyl group at carbon atom 3 is U.S. Pat. No. 3,413,287. Other documents describing estrogenic or hormonal effects of non-aromatic streroids with 3-hydroxyl substitution and a 4–5 double bond are WO 94 18224, U.S. Pat. No. 3,465,010, FR 2099385, U.S. Pat. No. 3,652,606 and EP 145 493. A document in which non-aromatic steroids with 3-keto substitution and a 5–10 double bond are disclosed is Baran et al (U.S. Pat. No. 3,377,366. Such compounds are described in general terms as agents with, among other, estrogenic or anti-estrogenic effects. Recently, in the field of drugs for estrogen receptors (ER) attention is focussed on the discovery of two distinct types of estrogen receptors, denoted ERα and ERβ (Mosselanan et al., *FEBS Letters* 392 (1996) 49–53 as well as EP-A-0 798 378). Since these receptors have a different distribution in human tissue, the finding of compounds which possess a selective affinity for either of the two is an important technical progress, making it possible to provide a more selective treatment of estrogen-deficiency related disorders, with a lower burden of estrogen-related side-effects.

BRIEF SUMMARY OF THE INVENTION

This invention provides estrogens satisfying the general formula

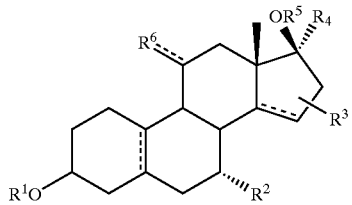

in which
- $R^1$ is H, $(C_1-C_3)$alkyl or $(C_2-C_3)$acyl;
- $R^2$ is H, α-$(C_1-C_4)$alkyl, α-$(C_2-C_4)$alkenyl or α-$(C_2-C_4)$alkynyl;
- $R^3$ is H or $(C_1-C_4)$alkyl, $(C_2-C_4)$alkenyl or $(C_2-C_4)$alkynyl, each at location 15 or 16 of the steroid skeleton;
- $R^4$ is H or $(C_1-C_5)$alkyl, $(C_2-C_5)$alkenyl or $(C_2-C_5)$alknyl, each optionally substituted with halogen; preferred is ethynyl;
- $R^5$ is H, $(C_1-C_3)$alkyl or $(C_2-C_3)$acyl;
- $R^6$ is $(C_1-C_5)$alkyl, $(C_2-C_5)$alkenyl, $(C_2-C_5)$alkynyl or $(C_1-C_5)$alkylidene, each optionally substituted with halogen or $(C_1-C_3)$alkyloxy; allyl is preferred; preferred halogens in $R^6$ are fluorine and chlorine.

Dotted bonds represent optional double bonds. When $R^6$ is alkylidene, the dotted line to $R^6$ represents the additional bond present in an alkylidene moiety, and when $R^6$ is alkyl or alkenyl, the bond from atom 11 to $R^6$ is a single bond.

It has been found that these non-aromatic estradiol derivatives with a substituent at the 11 position of the steroid skeleton possess selective affinity for the ERα-receptor.

The compounds according to the present invention are suitable as improved estrogens, in the sense that they can be used in estrogen-related disorders, such as menopausal complaints and osteoporosis. Utility they also find in contraception, and they further may be suitable in the treatment or prevention of Alzheimer's desease, breast tumor, benign prostate hypertrophy, and cardiovascular disorders. The compounds of the invention are particularly suitable in the treatment and prevention of estrogen-deficiency related disorders under diminished estrogen-related side-effects.

DETAILED DESCRIPTION OF THE INVENTION

In this description terms have the following meaning:
- $(C_1-C_5)$alkyl is a branched, unbranched or cyclized alkyl group having 1–5 carbon atoms, for example methyl, ethyl, isopropyl, 2-methylcyclopropyl, butyl, sec-butyl, tert-butyl etc.;
- $(C_2-C_5)$alkenyl is a branched, unbranched or cyclized alkenyl group having 2 to 5 carbon atoms, such as ethenyl, 2-butenyl, etc.
- $(C_2-C_5)$alkynyl is a branched or unbranched alkynyl group having 2–5 carbon atoms, such as ethynyl and propynyl.
- $(C_2-C_3)$acyl is a group having 2–3 carbon atoms and derived from an alkylcarboxylic acid, the alkyl moiety having the meaning as defined previously.
- $(C_1-C_5)$alkylidene is a branched, unbranched or cyclized alkylidene group having 1–5 carbon atoms, such as methylene and ethylene.

Within the general formula given above, the compounds of the invention preferably are those satisfying the general formula II,

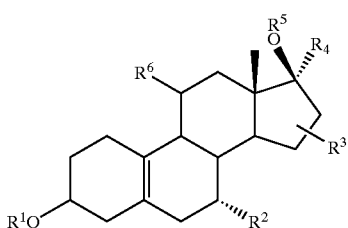

formula II in which
- $R^1$ is H, $(C_1-C_3)$alkyl, $(C_2-C_3)$acyl;
- $R^2$ is H, α-$(C_1-C_4)$alkyl, α-$(C_2-C_4)$alkenyl, α-$(C_2-C_4)$alkynyl;
- $R^3$ is H or $(C_1-C_4)$alkyl at location 16 of the steroid skeleton;
- $R^4$ is ethynyl
- $R^5$ is H or $(C_1-C_3)$alkyl, $(C_2-C_3)$acyl;
- $R^6$ is $(C_1-C_5)$alkyl, $(C_2-C_5)$alkenyl, $(C_2-C_5)$alkynyl; each can be substituted with chlorine or fluorine. When $R^6$ is ($C_1$–$C_2$)alkyl, ethenyl or ethynyl, each optionally substituted with chlorine or fluorine, it is preferred that $R^3$ is methyl at location 16 of the steroid skeleton.

More preferred are the steroids of the invention in which, in the above general formula II, $R^1$ is H;

$R^2$ is H;

$R^3$ is H or 16 α-methyl;

$R^4$ is ethynyl;

$R^5$ is H;

$R^6$ is propenyl, allyl or butenyl.

The compounds of the invention may be produced by various methods known in the art of organic chemistry in general, and especially in the art of the chemistry of steroids. See for example: Fried, J. and Edwards, J. A., "*Organic Reactions in Steroid Chemistry*", Volumes I and II, Van Nostrand Reinhold Company, N.Y., 1972; and C. Djerassi "Steroid Reactions", Holden-Day, Inc., San Francisco, 1963.

Synthesis of steroids with particular substituents at the C7 position are e.g. available via conjugate additions of organometallic species to appropriate 4,6-diene-3-one steroids, generally producing the 7α derived steroids (along with minor amounts of 7β steroids which can easily removed via crystallisation or chromatography. Many examples of which are known from literature. Introduction of substituents at the C11 position of the steroid skeleton can be performed in several ways. Conjugate addition of organometallic species to a suitably protected 5α,10α-epoxy, 9(11)-olefin as described by Teutsch et al, Steroids 37, 361 (1981) is such an approach, but other methods, using the 11-oxo functionality of an adequately protected 19-norandrost-5-ene as a reactive functionality for functional group interconversion to e.g. a C11-aldehyde according to well known chemical methodology (see a.o. E. Ottow et al., Tetr. Lett., 5253 (1993)) may be used as well to end up with claimed compounds. Of course a combination of both approaches outlined serves similarly well to achieve the goals. Introduction of a double bond at the 5(10) position is accomplished either by application of the so-called Birch reduction of the A ring of aromatic counterparts of suitably functionalized steroids, by dissolving metal reduction of Δ-4,5–9, 11-dienones, or by ketalization of 3-keto-Δ-4,5-steroids. This latter procedure leads either directly to the desired selective Δ-5(10)-isomers or leads to mixtures of ketals which can be separated via chromatography or crystallization at appropriate stages of the synthesis. Careful hydrolysis of the ketal at C3 generally affords the desired 3-oxo-Δ-5(10)-isomers, which can be converted into the 3-OH compounds by hydride reductions. Saturated steroids (i.e. 5αH-derivatives ) are easily available under reductive conditions like dissolving alkali metals in amines or ammonia. Introduction of double bonds at C14,15 is generally performed by firstly introducing a double bond at the C15,C16 position, followed by isomerization of this bond to the C14,C15 position according to well known procedures. The double bond introduced at C15,C16 may alternatively be used to perform a conjugate addition with e.g. cyanide, to allow the further construction of substituents at C15. The introduction of C16 substitution is easily performed by alkylation with appropriate bases and electrophiles.

The present invention also relates to a pharmaceutical composition comprising the steroid compound according to the invention mixed with a pharmaceutically acceptable auxiliary, such as described in the standard reference Gennaro et al., *Remington's Pharmaceutical Sciences*, (18th ed., Mack publishing Company, 1990, see especially Part 8: Pharmaceutical Preparations and Their Manufacture.). The mixture of the steroid compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants. polymeric binders and the like is contemplated. In general any pharmaceutically acceptable additive which does not interfere with the function of the active compounds can be used. The steroid compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the steroid compound according to the invention for the manufacture of a medicament in the treatment of estrogen-deficiency related disorders such as peri- and/or post-menopausal complaints. Thus the invention also pertains to the medical indications of peri- and/or post-menopausal (climacteric) complaints and osteoporosis, i.e. a method of treatment in the field of HRT (hormone replacement therapy), comprising the administration to a patient, being a woman, of a compound as described hereinbefore (in a suitable pharmaceutical dosage form).

Further, the invention relates to the use of the steroid compound according to the invention in the manufacture of a medicament having contraceptive activity. Thus the invention also pertains to the medical indication of contraception, i.e. a method of contraception comprising the administration to a subject, being a woman or a female animal, of a progestogen and an estrogen as is customary in the field, wherein the estrogen is a compound as described hereinbefore (in a suitable pharmaceutical dosage form).

Finally the invention relates to the use of the steroid compound for the manufacture of a medicament having selective estrogenic activity, such a medicament being generally suitable in the area of HRT (hormone replacement therapy).

The dosage amounts of the present steroids will be of the normal range for estradiol derivatives, e.g. of the order of 0.01 to 10 mg per administration.

The invention is further illustrated hereinafter with reference to some unlimitative Examples and the corresponding formula schemes referred to.

EXAMPLE 1

The synthesis of compounds (3α,11β,17β)-11-(2-propenyl)-19-norpregn-5(10)-en-20-yne-3,17-diol (compound 11) and (3α,11β,16α,17β)-16-methyl-11-(2-propenyl)-19-norpreg-5(10)-en-20-yne-3,17-diol (compound 16) is described with reference to scheme 1 (next page). Compounds are referred to by numbers. The numbers refer to corresponding structural formulas in the schemes 1–7

Compound 2

To a solution of 17.3 g of CuI and 3.84 g of LiCl in 250 ml of dry THF was added at −70° C. 90.6 ml of a 1M solution of allylmagnesium bromide in diethyl ether. After stirring for an additional 20 min. 11.4 ml of trimethylchlorosilane was added followed by a solution of 7.5 g of steroid 1 in 100 ml of THF. The reaction mixture was kept all the time below −60° C. After stirring for 1 h the reaction was quenched by pouring into sat. aquous NH₄Cl solution. The product was extracted with ethyl acetate and subsequently purified by column chromatography to provide 6.25 g of 2 as a colorles oil. NMR 5.20 (m, CH allyl); 5.0 (CH$_2$, allyl); 3.04 (m, H11).

3

To a solution of 9.6 g of 2 in a mixture of 100 ml of methanol and 30 ml of methylene chloride, containing 800 mg of NaOH, was added 0.4 g of sodium borohydnrde at 0–5° C. After stirring for 1.5 h the reaction was complete and the mixture was treated with 20 ml of acetone for 0.5 h.

The reaction was then poured into water and extracted with ethyl acetate, to provide 9.5 g of 3. NMR-3.59 (t, CHOH); 2.98 (m, H11), 0.92 (s, CH$_3$).

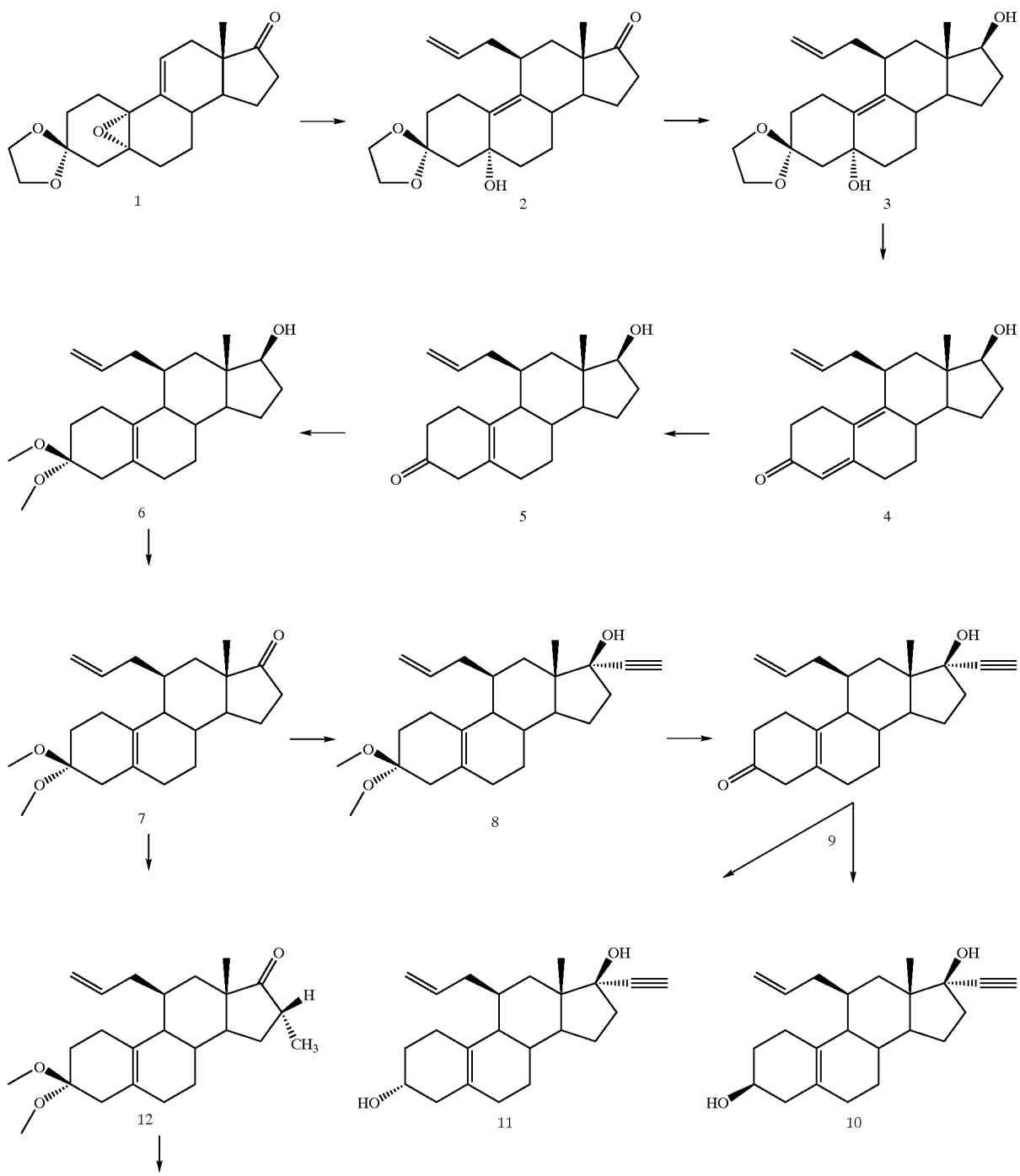

Scheme I

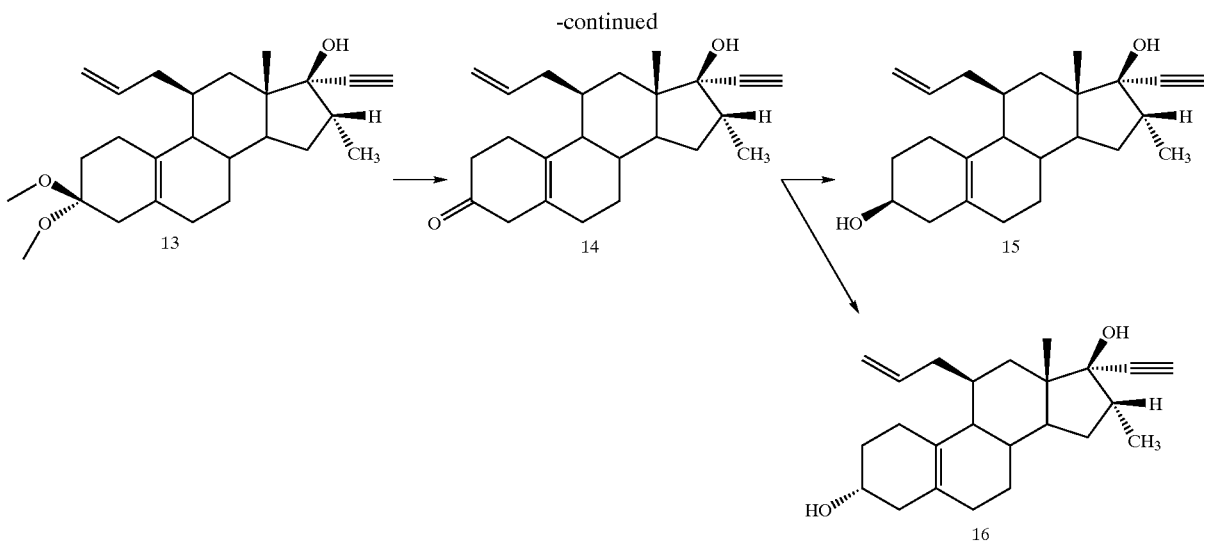

4

To a solution of 9.5 g of 3 in 100 ml of acetone was added 8 ml of 6 N HCl. After stirring for 2 h. The mixture was neutralized with NaHCO3 and concentrated to a small volume diluted with water and extracted with ethyl acetate. This provided 8.2 g of 4 as a colorless amorphous material. NMR 5.68 (m, H4); 3.10 (m, H11); 3.65 (m, CHOH).

5

A solution of 8.2 g of 4 in 100 ml of dry THF was added to 500 ml of liq. NH3 at −70° C. This mixture was treated with an amount of lithium metal (about 500 mg) until the blue color of the reaction mixture persisted for at least 15 min. The reaction was quenched by addition of a portion of $NH_4Cl$. The residue which remained after evaporation of the $NH_3$ was diluted with water and extracted with ethyl acetate. Chromatographic purification provided 4.0 g of 5 as a colorless oil.; $R_f$ 0.55 (hept./ethylacetate 1/1 v/v).

NMR 2.80 (ab, CH2 at C4); 0.93 (s, $CH_3$).

6

To a solution of 4.0 g of 5 in 80 ml of methanol was added 6 ml of trimethylorthoformate, followed by 0.8 g of toluenesulfonic acid. After stirring for 2 hr the ketafization was completed. The mixture was treated with 6 ml of pyridine and concentrated to a small volume. The remainders were diluted with water and extracted with ethyl acetate. The residue 4.7 g, consisted of almost pure 6; tlc, $R_f$ 0.78 (hept./ethylacetate 1/1, v/v).

NMR 3.22, 3.25 (2xs, $OCH_3$).

7

To a solution of 33 g of 6 in 50 ml of acetone was added 6 gr of mol sieves (4A) followed by 3.2 g of N-methylmorpholine-N-oxide and 150 mg of tetrapropylammonium perruthenate. The mixture was stirred for 1 h. To the reaction mixture was added 5 g of silica gel followed by 50 ml of heptane and was stirred for an additional 5 min. The mixture was filtered over hy-flow, and after concentration in part it was taken up in ethylacetate, washed with water, and concentrated. The residue was passed over a short silica column and provided 2.9 g of 7. $R_f$ 0.52 (heptane/ethylacetate 7/3). NMR 1.02 (s, $CH_3$).

8

For the ethinylation lithiumacetylide was prepared from dibromoethene and butyllithium. To a solution of 0.74 ml of 1,2-dibromoethene in 20 ml of THF was added at −70° C. 11 ml of a 1.6 M solution of BuLi in hexane. After stirring for 15 min. a solution of 800 mg of 7 in 2 ml of THF was added. The mixture was allowed to warm to room temperature in 15 min, and after an additional 15 min. at room temperature the reaction was quenched with water and the product extracted with ethyl acetate. Concentration followed by passing through a short silica gel column gave 810 mg of 8 as a white amorphous material. $R_f$ 0.48 (heptane-ethyl acetate 7/3), $R_f$ starting material 0.52. NMk 2.61 (s, acetylene).

9

To a suspension of 3.2 g of 8 in 60 ml of ethanol was added 0.16 g of oxalic acid in 16 ml of water. The mixture was stirred for 2.5 hr and became gradually homogeneous. The reaction mixture was treated with $NaHCO_3$ and concentrated to a small volume. Then water was added And the product was extracted with ethyl acetate. The crude product thus isolated was passed through a short silca gel column and crystallized from diisopropylether, to provide 2.3 g of 9, Mp 136° C. $R_f$ 0.66 (heptane-ethyl acetate 1/1). NMR 2.78 (ab, 2, H4); 2.61 (s, acetylene).

10, 11

To a solution of 1 g of 9 in 12 ml of THF was added 1.6 g of lithium tri-t-butoxy-aluminumhydride. After stirring for 1 h at room temperature the mixture was treated with water and neutralized by addition of 2N HCl. The product was extracted with ethyl acetate and chromatographed over silicagel (heptane/ethylacetate 8/2 as eluent). This provided 0.56 g of 3β alcohol 10 (Mp 121–123° C.) and 0.24 g of 3α alcohol 11 (Mp 84–87° C.).

$R_f$ 0.53 (10) and 0.45 (11), heptane/ethylacetate 1/1. No (3αOH) 3.82 (m, CHOH); (3βOH) 4.08 (m, CHOH)

12

To a solution of lithium hexamethyldisilazide (prepared from 1.9 ml of 1.6M BuLi-hexane solution and 0.71 ml of hexamethyldisilazane in 4 ml of dry THF) was added at −40° C. 1 g of 7 and 0.7 ml of DMPU in 5 ml of THF. The mixture was stirred for 0.5 hr at −40° C. and then 225 ul of $CH_3I$ was added by syringe. After stig for an additional 0.5 h at −40° C. the reaction was completed. The mixture was diluted with water and extracted with ethylacetate. Chrornatography of the crude product thus isolated gave 1.3 gr of 12, $R_f$ 0.43 (heptane/ethylacetate 8/2).

13

According to the procedure described for the preparation of 8, 1.3 g of 12 were converted into the required 13, to provide 1.2 g, $R_f$ 0.46 (heptane/ethylacetate 7/3) $R_f$(12) 0.55.

14

To a solution of 800 mg of 13 in 20 ml of ethanol was added a solution of 80 mg of oxalic acid in 5 ml of water. The mixture was stirred for 1 h and then neutralized by addition of NaHCO₃. After dilution with water and extraction with ethylacetate 0.7 g of 14 remained as crystalline material. $R_f$ 0.47 (heptane/ethylacetate 7/3).

15,16 fluoride. The mixture was stirred for 48 hr at ambient temperature and then poured into ice-water and extracted with methylenechioride. followed by washing with NaHCO₃. After concentration and chromatography (SiO₂-heptane-ethyl acetate 2/1) 2.5 g of 18 was obtained, Mp 138–139. NMR (CDCl₃) 6.05 ppm double triplet of CHF₂;, 5.9 s, H4; 0.95 (s, CH₃).

Scheme II

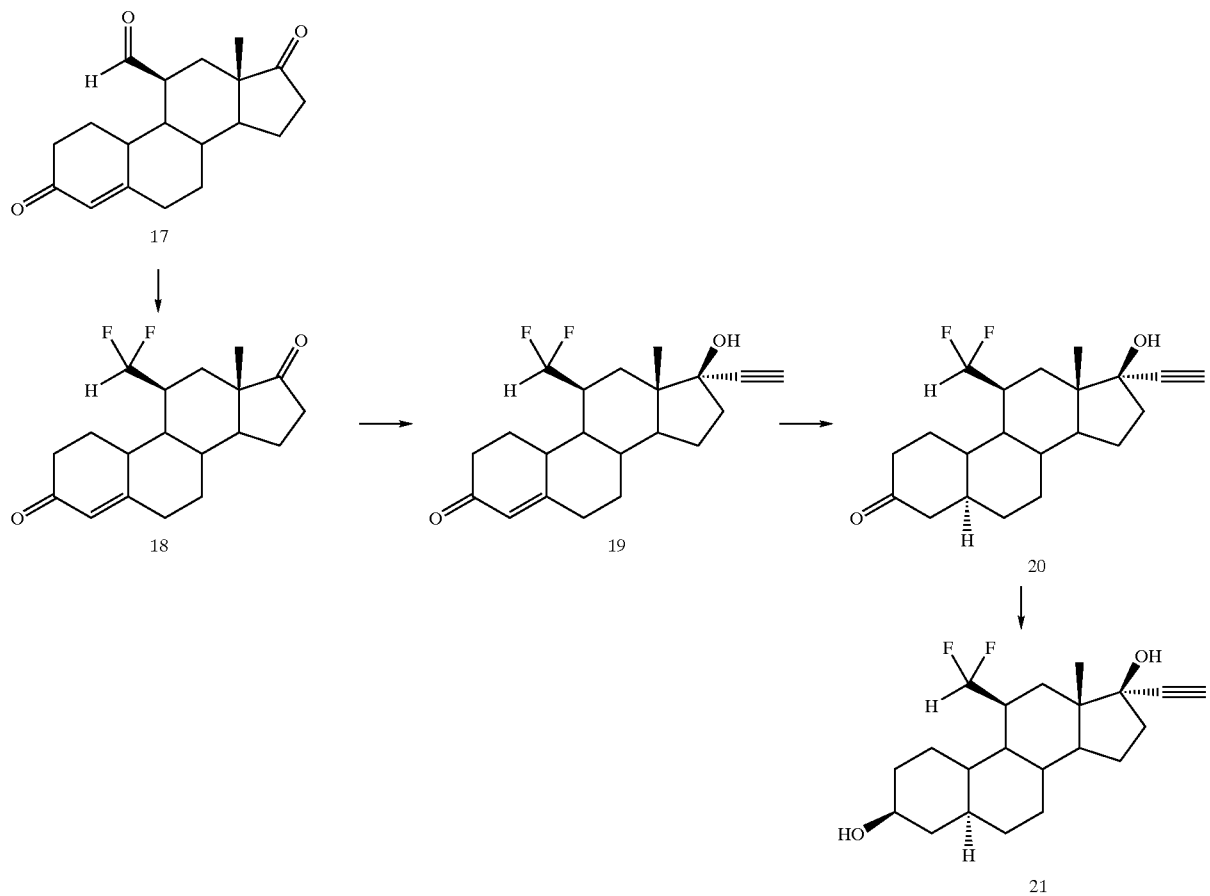

To a solution of 725 mg of 14 in 20 ml of a 1/1 mixture of ethanol and THF was added 130 mg of sodiumborohydride. After stirring for 1 h 2 ml of acetone were added to destroy sonme excess reagent. After 15 min the mixture was poured into water and the product was extracted with ethylacetate. The material thus obtained was purified by chromatography at silicagel, using either methylenechloride-acetone or hexane-ethylacetate as eluent. This gave 300 mg of 16 (3α-OH) and 75 mg of 15 (3β-OH). $R_f$ (15) 0.47 (methylenechloride/acetone 95/5). $R_f$ (16) 0.54 (methylenechloride/acetone 95/5)

EXAMPLE 2

The synthesis of the compound (3β,5α,11β,17β)-11-difluoromethyl-19-norpregn-20-yne-3,17-diol (compound 21) is described with reference to scheme 2 (next page).

18

To a solution of 4 g of known aldehyde 17 in 200 ml of methylenechloride was added 10 ml of dimethylsulphurtri-

19

Acetylene gas was passed for 45 min into a degassed mixture of 1.3 g of potassium-tert.butoxide and 1 g of 18 in 7 ml of THF and 2 ml of tert.butanol at 0° C. The mixture was then poured into water and extracted with ethyl acetate. After washing and concentration, the residual material wwas treated with diisopropyl ether, to yield 0.85 g of 19 as white solid. Mp 178–180. $R_f$ 0.43 (heptane-ethylacetate 1/1).

20

To a solution of 20 mg of Li in 10 ml of liquid NH₃ was added at −60° C. a solution of 300 mg of 19 in 6 ml of THF. After stirig for 1 min the mixture was treated with 0.5 g of NH₄Cl. The NH₃ was evaporated and the residue treated with water and extracted with ethylacetate. The material thus obtained was purified by chromatography, to give 140 mg of 20, Mp 224–225, $R_f$ 0.64 (heptane-ethylacetate 7/3).

21

To a solution of 25 mg of LiAlH₄ in 4 ml of THF was added at −60° C. 85 mg of 20 in 1 ml of THF. After stiring for 5 min the mixture was quickly warmed to RT and worked up by addition of 45 μl of water, 45 μl of 3N NaOH solution and 140 μl of water. The precipitates were filtered and the filtrate taken up in ethylacetate and washed with 2N HCl and water. The residue which remained after drying and concentration was triturated with diisopropyl ether and gave 50 mg of 21. Mp 168–169° C., R$_f$ 0.30 (toluene-ethylacetate 7/3) NMR 3.6 ppm CHOH, 2.65 CH acetylene, 6.0 double triplet CHF$_2$).

EXAMPLE 3

The synthesis of the compounds (3β,5α,11β,17β)-11-(2-fluoroethyl)-19-norpregn-20-yne-3,17-diol (compound 31) and (3α,5α,11β,17β)-11-(2-fluoroethyl)-19-norpregn-20-yne-3,17-diol (compound 32) is described with reference to scheme 3.

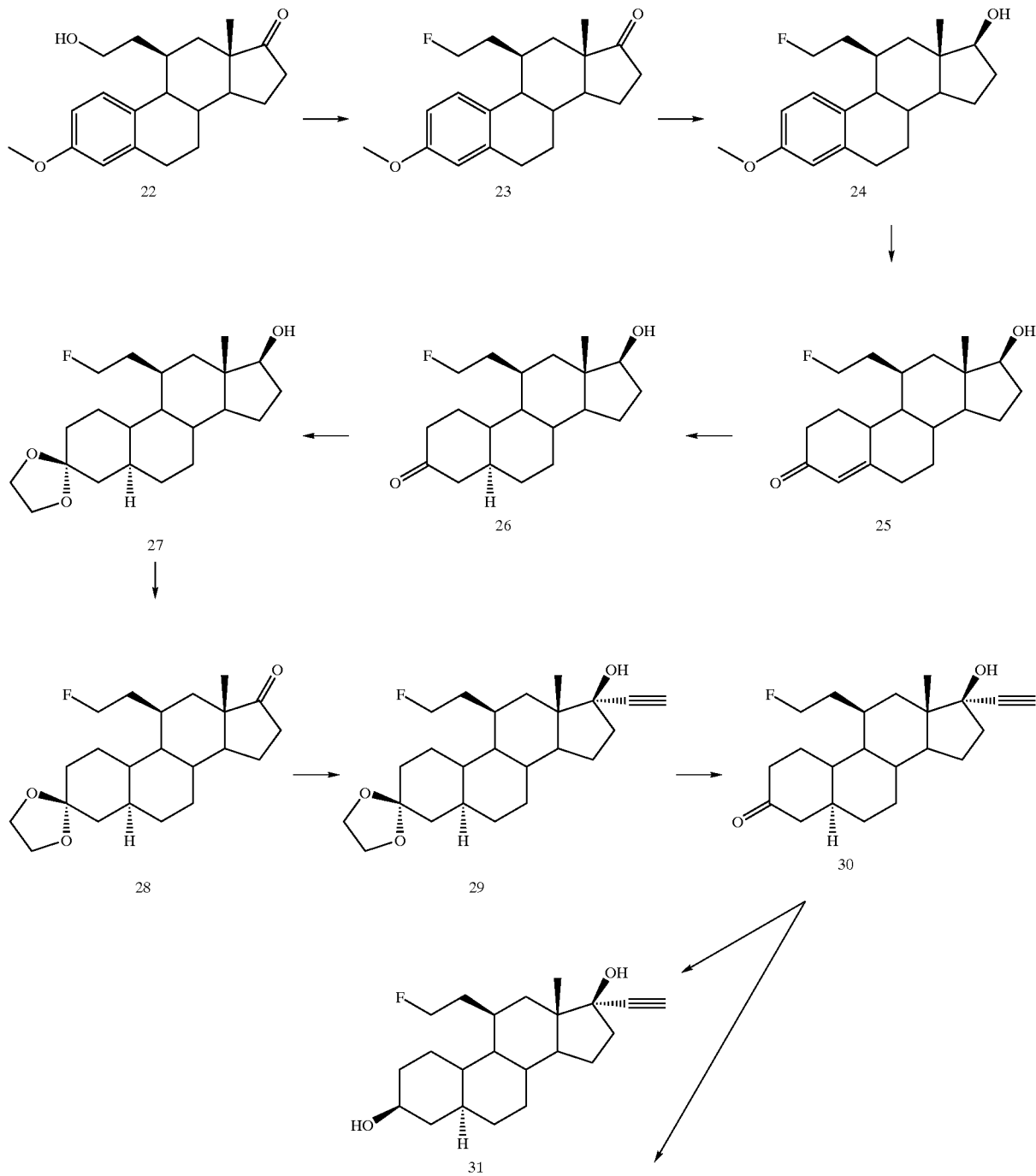

Scheme III

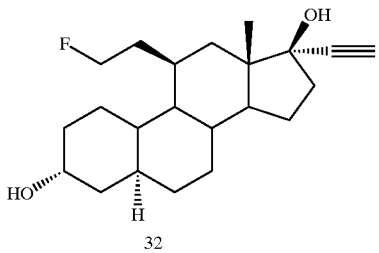

32

23

To a solution of 4.95 g of 11β-hydroxyethylestrone-3-methylether (22) in 115 ml of THF was added 66 g of mol sieves 4A, followed by 45 ml of 1M TBAF in THF (dry) and then 5.3 g of tosyffluoride. The mixture was stirred and refluxed for two hour. Then the reaction was cooled and poured onto 700 ml of 10% aq $NaHCO_3$ solution and extracted with ethyl acetate. After concentration of the solvent and chromatography 3.4 g of 23 were isolated. $R_f$ 0.39 (heptane/ethylacetate 7/3).

24

A solution of 4 g of 23 in a mixture of 30 ml of THF and 30 ml of methanol was treated with 0.1 ml of 4 N NaOH and then with 0.23 g of $NaBH_4$. After stirring for 1 h the reaction was poured into water and extracted with ethylacetate. The crude material was filtered through a short silacolumn to provide 3.8 g of 24. $R_f$ 0.26 (heptane/ethyl acetate 7/3) $R_f$ 23: 0.33.

25

To a solution of 3.8 g of 24 in a mixture of 40 ml of THF and 230 ml of liq $NH_3$ was added at –33° C. 5 g of Li. The mixture was stirred for 5 h. Then excess lithium was destroyed by treatment with 45 ml of ethanol. Ammonia was allowed to evaporate and the residue was diluted with water and extracted with ethylacetate. Upon drying and concentration 3.7 g of crude 1,2,5(10)dienolether were obtained. This was dissolved in 30 ml of acetone, to which 3 ml of 6N HCl were added. After stirring for 3 h the mixture was neutralized with $NaHCO_3$, followed by dilution with water and extraction with ethyl acetate, to provide 2.8 g of 25. $R_f$ 0.10 (heptane/ethyl acetate 4/6).

26

A solution of 0.84 g of 25 in a mixture of 30 ml of liq $NH_3$ and 6 ml of THF was treated at –60° C. with small pieces of littium until a blue color of the reaction mixture persisted for at least 5 min. Then excess reagent was destroyed by addition of a small amount of $NH_4Cl$ and $NH_3$ was evaporated. The residual material was diluted with water and extracted into ethyl acetate. Concentration of the solvent left 0.80 g of essentially pure matyerial; $R_f$ (0.39 (heptane/ethyl acetate 1/1), $R_f$ 25. 0.24.

27

To a solution of 0.8 g of 26 in 8 ml of dichloromethane was added 2.8 ml of ethyleneglycol, 2,5 ml of triethylorthoformate and 5 mg of toluenesulfonic acid. The mixture was stirred overnight and then poured onto sat.$NaBCO_3$ solution and extracted with ethylacetate. The crude material thus obtained was purified by passing through a short silica gel column, to provide 0.72 g of 27. $R_f$ 0.46 (heptane/ethyl acetate 1/1), $R_f$ 26, 0.38.

28

To a solution of 0.72 g of 27 in 15 ml of acetone was added 1 gr of mol sieves (4A) followed by 0.70 g of N-methylmorpholine-N-oxide and 30 mg of tetrapropylammonium perruthenate. The mixture was stirred for 1 h. To the reaction mixture was added 1 g of silica gel followed by 15 ml of heptane and was stirred for an additional 5 min. The mixture was filtered over hy-flow, and after concentration in part it was taken up in ethylacetate, washed with water, and concentrated. The residue was passed over a short silica column and provided 0.59 g of 28. $R_f$ 0.62 (heptane/ethylacetate 1/1).

29

For the ethinylation lithiumacetylide was prepared from dibromoethene and butyllithium. To a solution of 0.74 ml of 1,2-dibromoethene in 20 ml of THF was added at –70° C. 11 ml of a 1.6 M solution of BuLi in hexane. After stig for 15 min. a solution of 590 mg of 28 in 2 ml of THF was added. The mixture was allowed to warm to room temperature in 15 min, and after an additional 15 min. at room temperature the reaction was quenched with water and the product extracted with ethyl acetate. Concentration followed by passing through a short silica gel column gave 430 mg of 29 as a white amorphous material. $R_f$ 0.11 (heptane-acetone 9/1), $R_f$ starting material 0.21.

30

To a solution of 0.43 g of 29 in 15 ml of acetone was added 1 ml of 2N HCl. The mixture was stirred for 2 h and subsequently treated with sat aq $NaHCO_3$ solution, followed by extraction with ethylacetate., to provide 0.40 g of essentially pure 30; $R_f$ 0.18 (heptane/ethyl acetate 7/3) $R_f$ 29 : 0.23.

31/32

To a solution of 040 g of 30 in 4 ml of THF and 4 ml of ethanol was added 30 mg of sodium borohydride. After stirring for 0.5 h a few drops of acetone were added to decompose excess reagent. After stirring for an additional 15 min the reaction was poured onto water and extracted with ethyl acetate and the crude material thus obtained was submitted to column chromatography to provide 80 mg of 3αOH isomer 32 and 160 mg of 3βOH derivative 31. $R_f$ 31: 0.37, $R_f$ 32: 0.42, $R_f$ starting mat. 0.48 (heptane/acetone 6/4).

EXAMPLE 4

The synthesis of the compounds (3α,11β,17β)-11-(3-butenyl)-19-norpregn-5(10)-en-20-yne-3,17-diol (compound 42) and (3β,11β,17β)-11-(3-butenyl)-19-norpregn-5(10)-en-20-yne-3,17-diol (compound 43) is described with reference to scheme 4.

Scheme IV

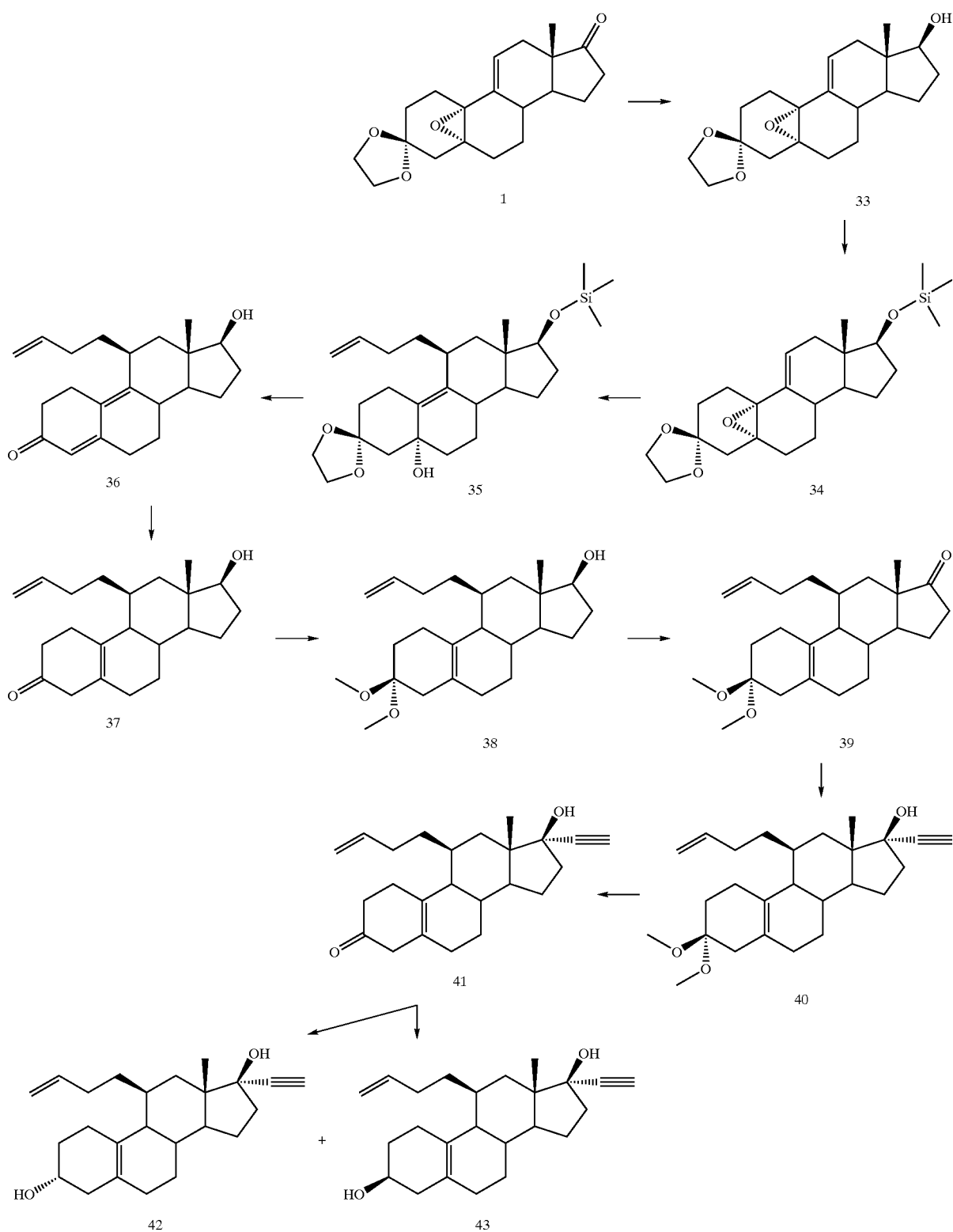

33

A solution of 55 g of steroid 1 in a mixture of 300 ml of THF and 300 ml of methanol was treated with a solution of 2.7 g of sodium borohydride in 30 ml of water (containing 3 mg of NaOH). After stirring for 1 h the reduction was completed and excess hydride was destroyed by addition of 75 ml of acetone. After stirring for an additional 1 h the reaction mixture was poured onto water and extracted with ethyl actetate. Concentration of the organic phase provided 54 g of 33, $R_f$ 0.31 (heptane/ethylacetate 4/6), $R_f$ starting material 0.42.

34

To a solution of 54 g of 33 in 350 ml of DMF was added 35 g of imidazole, followed by 37 ml of trimethylsilyl chloride at −10° C. After stirring for an additional 0.5 h the reaction was complete. The mixture was poured into 1.5 l of water and extracted with ether. The residueobtained after concentration of the organic material was triturated in 80% aq.ethanol to provide 50 g of pure 34, Mp 90–91° C., $R_f$ 0.79 (heptane/ethylacetate 4/6), $R_f$ starting material 0.36

35

To a solution of butenylmagnesium bromide, prepared from 0.51 ml of 4-bromo-1-butene and 119 mg of Mg in 20 ml of THF was added at −10° C. 100 mg of CuI. After stirring for 0.5 h the mixture was cooled to −30° C. and 1 g of 34 in 5 ml of THF was added. The reaction mixture was allowed to reach room temperature in about 1 h. Then 100 ml of sat. aq NH$_4$Cl solution was added followed by extraction with ethylacetate. Chromatography provided 0.9 g of 35. $R_f$ 0.54 (heptane/ethylacetate 6/4), $R_f$ starting material 0.60.

36

To a solution of 8.65 g of 35 in 80 ml of acetone was added 2 ml of 2N HCl. The mixture was stirred for 2 h and subsequently neutralized with sat aq NaHCO$_3$ solution, concentrated to a small volume, diluted with water followed by extraction with ethylacetate. The crude material thus obtained was passed through a short silica gel column, to provide 5.3 g of 36; $R_f$ 0.18 (heptane/ethyl acetate 7/3) $R_f$ starting material 0.51.

37

Small pieces of lithium metal were added to a solution of 5.3 g of 36 in a mixture of 340 ml of liq. NH$_3$, 110 ml of THF and 9 ml of t-butanol at −70° C. until the blue color persisted (±350 mg) for 45 min. Excess reagent was destroyed by addition of NH$_4$Cl. Ammonia gas was evaporated and the residue diluted with water and extracted with ethyl acetate. The crude material thus obtained was passed through a short silica gel column to provide 3.8 g of 37. $R_f$ 0.46 (heptane/ethyl acetate 6/4) $R_f$starting material 0.22.

38

To a solution of 3.3 g of 37 in 60 ml of methanol was added 5 ml of trimethylorthoformate and 0.3 g of p-toluenesulforiic acid. After stirring at roomtemperature for 1 h the mixture was neutralized by addition of 1 ml of pyridine. The mixture was concentrated to one third of the original volume and poured into water and extracted with ethyl acetate, providing 3.7 g of 38 after chromatographic purification. $R_f$ 0.60 (heptane/ethyl acetate 1/1) Restarting material 0.48.

39

To a solution of 3.7 g of 38 in 45 ml of acetone was added 5 gr of mol sieves (4A) followed by 3.6 g of N-methylmorpholine-N-oxide and 100 mg of tetrapropylammonium perruthenate. The mixture was stirred for 1 h. To the reaction mixture was added 5 g of silica gel followed by 100 ml of heptane and was stirred for an additional 5 min. The mixture was filtered over hy-flow, and after concentration in part it was taken up in ethylacetate, washed with water, and concentrated. The residue was passed over a short silica column and provided 3.3 α of 39. $R_f$ 0.51 (heptane/ethylacetate 7/3); starting material $R_f$ 0.38.

40

For the ethinylation lithiumacetylide was prepared from dibromoethene and butyllithium.

To a solution of 0.74 ml of 1,2-dibromoethene in 20 ml of THF was added at −70° C. 11 ml of a 1.6 M solution of BuLi in hexane. After stirring for 15 min. a solution of 0.8 g of 39 in 2 ml of THF was added. The mixture was allowed to warm to room temperature in 15 min, and after an additional 15 min. at room temperature the reaction was quenched with water and the product extracted with ethyl acetate. Concentration followed by passing through a short silica gel column gave 0.96 g of 40 as a white amorphous material. $R_f$ 0.15 (heptane-acetone 95/5), $R_f$ starting material 0.30

41

To a solution of 0.95 g of 40 in 20 ml of ethanol was added 0.6 g of oxalic acid in 3 ml of water. The mixture was stirred for 1.5 hr. The reaction mixture was treated with NaHCO$_3$ and concentrated to a small volume. Then water was added, and the product was extracted with ethyl acetate. The crude product thus isolated was passed through a short silica gel column, to provide 0.55 g of 41. $R_f$ 0.33 (heptane-ethyl acetate 7/3); $f_f$starting material 0.40.

42/43

To a solution of 0.55 g of 41 in 4 ml of THF and 4 ml of ethanol was added 30 mg of sodium borohydride. After stirring for 0.5 h a few drops of acetone were added to decompose excess reagent. After stirring for an additional 15 min the reaction was poured onto water and extracted with ethyl acetate and the crude material thus obtained was submitted to column chromatography to provide 90 mg of 3αOH isomer 42, Mp 159° C., and 150 mg of 3βOH derivative 43,Mp 90° C. $R_f$ 42: 0.31, $R_f$ 43: 0.23, $R_f$ starting material 0.41 (heptane/ethyl acetate 6/4).

EXAMPLE 5

The synthesis of the compounds (3β,7α,11β,17β)-11-(2-fluoroethyl)-7-methyl-19-norpregn-5(10)-en-20-yne-3,17-diol (compound 54) and (3α,7α,11β,17β)-11-(2-fluoroethyl)-7-methyl-19-norpregn-5(10)-en-20-yne-3,17-diol (compound 55) is described with reference to scheme 5 (next page).

45

To a solution of 4 g of 44 in 35 ml of methanol was added 12 ml of trimethyl orthoformate, followed by 0.3 g of toluenesulfonic acid. After stirring for 1 h starting material had been consumed, and the reactionmixture was neutralized by adding 1 g of NaHCO$_3$ and was concentrated. The residue was diluted with water and extracted with ethylacetate. Chromatography of the crude material gave 3.4 g of 45. $R_f$ 0.61 (heptane/ethylacetate 7/3). $R_f$starting material 0.35.

46

To a solution of 3.4 g of 45 in 50 ml of methanol was added 0.5 g of NaOH. After stirring for 2 h the saponification was complete. The mixture was concentrated, diluted with water and extracted with ethyl acetate, providing 3 g of 46 as a colorless oil. $R_f$ 0.31 (heptane/ethyl acetate 7/3). $R_f$ starting material 0.65.

47

To a solution of 3.6 g of 46 in 30 ml of DMF was added 2.8 g of imidazole, followed by 2 g of tert.butyldimethylsilyl chloride.After stirring for 2 h the mixture was poured into water and extracted with ethyl acetate. The crude material was passed through a short silica gel-column to-provide 3.8 g of 47 as an oil.

$R_f$ 0.70 (heptane/ethylacetate 7/3). $R_f$ starting material 0.61.

complex in 40 ml of THF. To this was added 3.8 g of 47 in 5 ml of THF. The mixture was stirred for 2 h and then

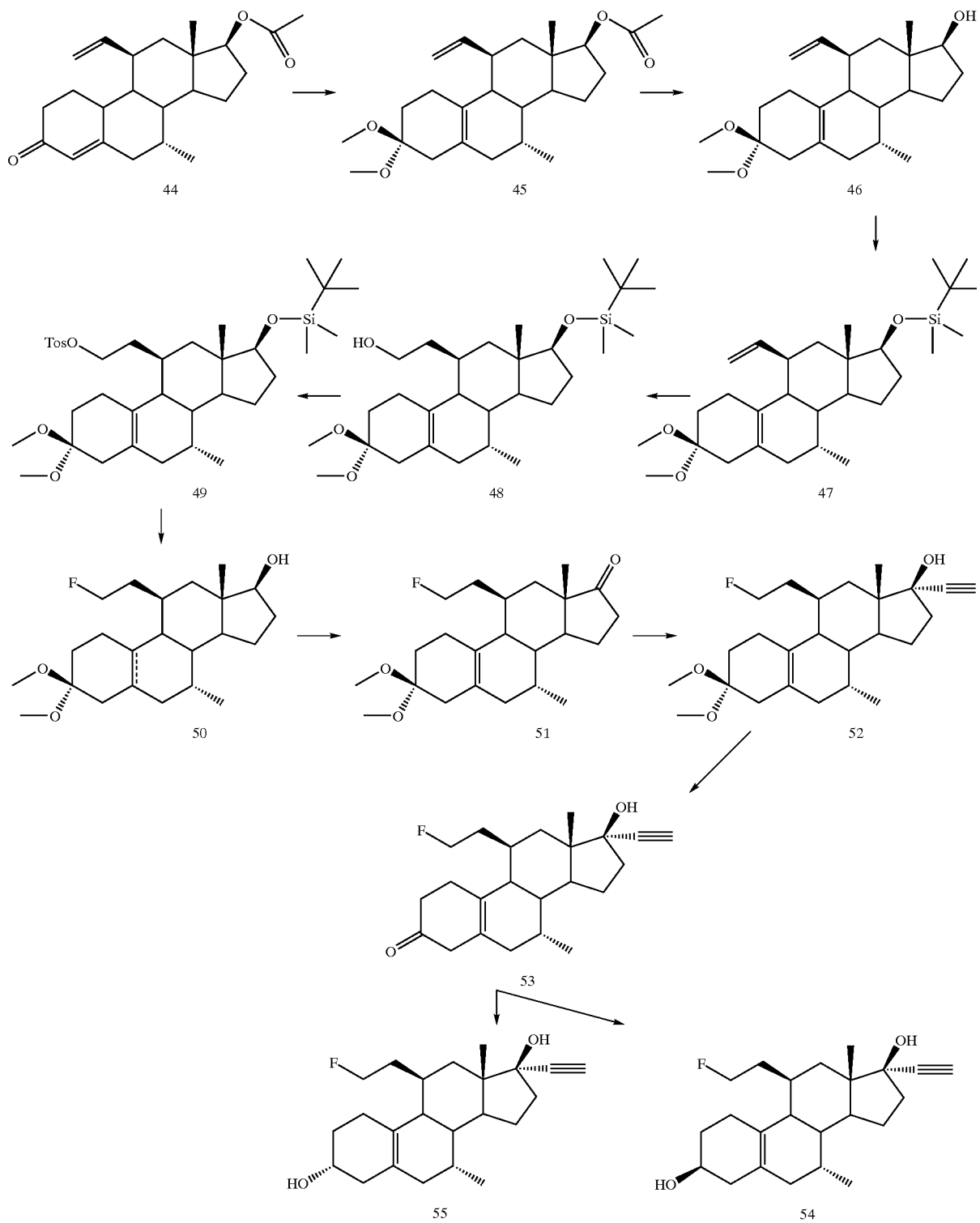

Scheme V

48

A solution of 9-BBN was prepared from 1.75 ml of 1,5-cyclooctadiene and 1.4 ml of borane-dimethylsulfide complex in 40 ml of THF. To this was added 3.8 g of 47 in 5 ml of THF. The mixture was stirred for 2 h and then quenched by careful addition of water (5 ml) followed by 10 ml of 2N NaOH and 8 ml of 30% $H_2O_2$. After vigorous stirring for 2 h the reaction mixture was further diluted with water, extracted with ethyl acetate and washed with 10% aq. Na$_2$SO$_3$ solution. Upon concentration and 10 chromatography 2.8 g of 48 were isolated. R$_f$ 0.27 (heptane/ethylacetate 7/3). R$_f$ starting material 0.70.

49

A mixture of 1 g of 48 and 0.5 g of tosyl chloride in 5 ml of pyridine was stirred for 5 h at 0–5° C. Then 1 ml of water was added and stirring prolonged for 15 min. The reaction mixture was further diluted with water and extracted with ethyl acetate and the crude product purified by chromatography, to provide 1.1 g of 49, Mp 120° C., R$_f$ 0.57 (heptane/ethylacetate 7/3). R$_f$ starting material 0.30.

50

A solution of 400 mg of 49 in 5 ml of dry 1M TBAF in THF was stirred for 5 h, leading to formation of the fluoride and concomitant cleavage of the silyl function. The mixture was poured into water and extracted with ethyl acetate. Purification by chromatography provided 185 mg of 50, Mp 161–162° C., R$_f$ 0.35(heptane/ethylacetate 7/3). R$_f$ starting material 0.53.

51

To a solution of 180 mg of 50 in 5 ml of acetone was added 0.5 gr of mol sieves (4A) followed by 200 mg of N-methylrnorpholine-N-oxide and 10 mg of tetrapropylammonium perruthenate. The mixture was stirred for 1 h. To the reaction mixture was added 0.5 g of silica gel followed by 10 ml of heptane and was stirred for an additional 5 min. The mixture was filtered over hy-foow, and after concentration in part it was taken up in ethylacetate, washed with water, and concentrated to give 150 mg of 51, Mp 166° C. R$_f$ 0.45 (heptane/ethylacetate 7/3); starting material R$_f$ 0.35.

52

For the ethinylation lithiumacetylide was prepared from dibromoethene and butyllithium.

To a solution of 0.30 ml of 1,2-dibromoethene in 6 ml of THF was added at −70° C. 4.5 ml of a 1.6 M solution of BuLi in hexane. After stirring for 15 min. a solution of 150 mg of 51 in 1 ml of THF was added. The mixture was allowed to warm to room temperature in 15 min, and after an additional 15 min. at room temperature the reaction was quenched with water and the product extracted with ethyl acetate. Concentration and treatment with some heptane provided 140 mg of 52 as a white solid, Mp 168° C. R$_f$ 0.38 (heptane-acetone 95/5), R$_f$ starting material 0.40.

53

To a solution of 145 mg of 52 in 3 ml of ethanol and 1.5 ml of THF was added 0.2 g of oxalic acid in 3 ml of water. The mixture was stirred for 1.5 hr. The reaction mixture was treated with NaHCO$_3$ and concentrated to a small volume. Then water was added, and the product was extracted with ethyl acetate. The crude product thus isolated was passed through a short silica gel column, to provide 125 mg of 53. R$_f$ 0.23 (heptane-ethyl acetate 7/3); R$_f$ starting material 0.38.

54/55

To a solution of 125 mg of 53 in 2 ml of THF and 1 ml of ethanol was added 20 mg of sodium borohydride. The reduction was complete after 0.5 h. The mixture was diluted with water and extracted with ethyl acetate. The crude product thus isolated was purified by passing through a reversed phase C-18 column, using acetonitrile-water as eluent, to provide 40 mg of 3αOH 55 and 20 mg of 3βOH 54, both as amorphous materials with identical R$_f$ values on silicagel; R$_f$ 0.43 (CH$_2$Cl$_2$/acetone 9/1), R$_f$ starting material 0.70.

EXAMPLE 6

The compounds in this example was prepared according to scheme VI (next page)

57

A solution of 80 mg of sodium borohydride and 112 mg of sodium hydroxide in 12 ml of methanol was added dropwise at 0° C. to a solution of 7α,11β-dimethylestr-4-ene-3,17-dione (56) in a mixture of 18 ml of methanol and 4 ml of methylenedichloride After stirring for one hour excess borohydride was destroyed by addition of 12 ml of acetone and stirring for an additional 15 min. The mixture was poured into water and extracted with ethyl-actate. The combined organic phases were once washed with sat NaCl solution and dried, concentrated and purified over a silica column, to provide 0.74 g of 57, contaminated with some 3,17-diol. (The latter one was removed in the next step); R$_f$ 0.40 (hept./ethyl ac. 6/4).NMR (CDCl$_3$) δ 3.60 (t, 1, 17αH), 0.77 (d, 3, 7αCH$_3$), 1.08 (d, 3, 11βCH$_3$).

58

To a solution of 0.74 g of 57 in 15 ml of methanol and 1.1 ml of trimethylorthoformate was added 0.2 g of p-toluenesulphonic acid. The mixture was stirred for 2 h. Then 0.1 ml of pyridine was added and poured onto water. The product was extracted with ethyl acetate and purified by chromatography over silica, using heptane/ethyl acetate as eluent, to provide 0.59 g of 3,3-dimethylketal 58, R$_f$ 0.47 (hept/ethylac. 6/4);NMR δ 3.20 (2 s, 6, OCH$_3$), 3.65 (t, 1, 17αH), 0.86 (s, 3, 18CH$_3$), 0.77 (d, 3, 7αCH$_3$), 0.90 (d, 3, 11βCH$_3$).

Scheme VI

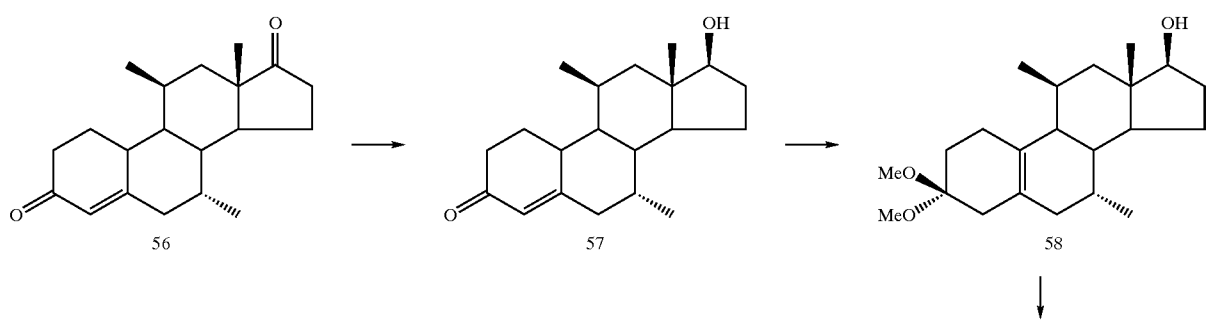

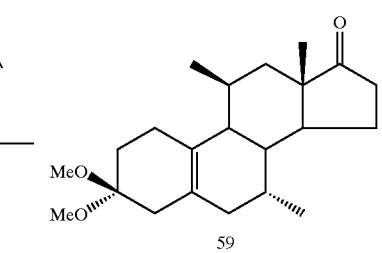
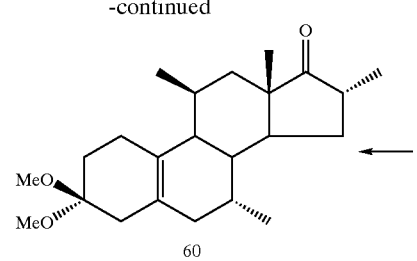
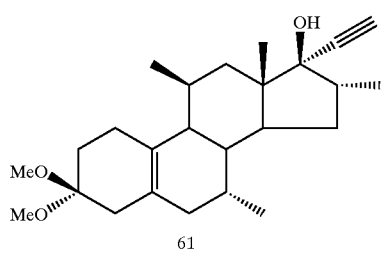

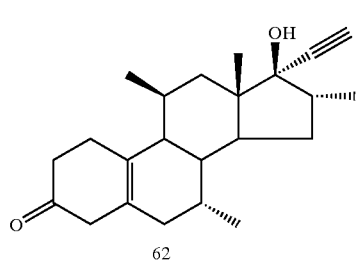
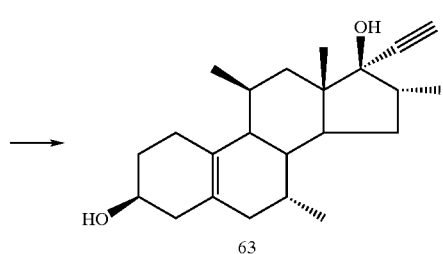

59

To a solution of 0.59 g of steroid 58 in 10 ml of acetone were added successively 0.6 g of N-methylrnorpholine-N-oxide and 40 mg of tetrapropylammonium perruthenate. After stirring for 1 h-10 ml of heptane and 1 g of silica were added. The mixture was stirred for an additional 15 min and then filtered over Celite, concentrated and the remainders passed over a short silica column, to provide 0.56 g of 59; $R_f$ 0.55 (hept./ethyl ac. 6/4); NMR δ 0.98 (s, 3, 18$CH_3$), 0.82 (d, 3, 7α$CH_3$), 0.92 (d, 3, 11β$CH_3$), 3.20 (2×s, 6, O$CH_3$).

60

Lithium hexamethyldisilazide was prepared by addition of 1.24 ml of 1.55 M BuLi-hexane solution at −40° C. to a solution of 0.44 ml of bistrimethylsilylamine in 4 ml of THF. After stirring for ½ h a solution of 0.56 g of 59 and 0.46 ml of DMPU in 8 ml of THF was added. Stirring was continued for 45 min at −40° C. followed by addition of 140 μl of methyliodide. Upon stirring for an additional 30 min the alkylation was complete. The mixture was poured into 40 ml of sat $NH_4Cl$ solution and extracted with ethyl acetate. Chromatographic purification provided 0.55 g of 16α-methylated product 60. $R_f$ 0.73 (hept/ethyl ac. 1/1)starting material $R_f$ 0.69; NMR δ 1.11 (d, 3, 16α$CH_3$), 1.02 (s, 3, 18$CH_3$), 0.82 (d, 3, 7α$CH_3$), 0.91 (d, 3, 11β$CH_3$).

61

Lithium acetylide was prepared by addition of a solution of 9.5 ml of 1.55 M BuLi-hexane to 0.60 ml of 1,2-dibromoethane in 20 ml of THF at −60° C. After stirring for ½ h, a solution of 0.55 g of ketone 60 in 2 ml of THF was added and the cooling device was removed so as to allow the mixture to gradually warm to room temperature. Then water was added and the product was extracted with ethylacetate. After chromatographic purification 0.50 g of 61 was obtained; $R_f$ 0.22 (hept/ethylac. 9/1) starting material $R_f$ 0.42; NMR δ 1.18 (d, 3, 16α$CH_3$), 1.02 (s, 3, 18$CH_3$), 0.78 (d, 3, 7α$CH_3$), 0.94 (d, 3, 11β$CH_3$), 2.66 (s, 1, acetylene).

62

To a solution of 0.49 g of 61 in 20 ml of ethanol was added 50 mg of oxalic acid in 3 ml of water. The mixture was stirred for 4 hr. The reaction mixture was treated with 5% aq.sodium bicarbonate solution and the product extracted with ethyl acetate and passed trough a silica column, to remove some impurities, yielding 250 mg of 62; $R_f$ 0.40 (hept/ethyl ac. 6/4), starting mat. $R_f$ 0.49; NMR δ 2.80 (m, 2, H4), 1.19 (d, 3, 16α$CH_3$), 1.04 (s, 3, $CH_3$), 0.82 (d, 3, 7α$CH_3$), 0.93 (d, 3, 11β$CH_3$), 2.67 (s, 1, acetylene).

63/64

To a solution of 240 mg of 62 in 5 ml of THF was added 360 mg of lithium(tert-butoxy)$_3$AlH. The mixture was stirred for 1 h, and then poured onto water and the product extracted with ethyl acetate. The isomeric alcohols thus obtained were separated by means of preparative hplc (reversed phase C18) using a gradient of acetonitrile/water. The products obtained after concentration of the eluent were crystallized from water-ethanol. This gave 68 mg of the 3α-hydroxy derivative 64, and 70 mg of the 3β-isomer 63, $R_f$ (63/64) 0.36 (hept/ethyl acetate 6/4), starting material $R_f$ 0.54. Mp (63) 165–167° C., Mp(64) 171–172° C. NMR (64) δ 3.80 (m, 1, H3), 2.67 (s, 1, acetylene), ), 1.17 (d, 3, 16α$CH_3$), 1.02 (s, 3, 18$CH_3$), 0.77 (d, 3, 7α$CH_3$), 0.90(d, 3, 11β$CH_3$). NMR (63) δ 4.05 (m, 1, H3), 2.67 (s, 1, acetylene), ), 1.18 (d, 3, 16α-$CH_3$), 1.02 (s, 3, 18$CH_3$), 0.77 (d, 3, 7α$CH_3$), 0.93(d, 3, 11β$CH_3$).

EXAMPLE 7
The compound in this example was prepared according to scheme VII (Next page):
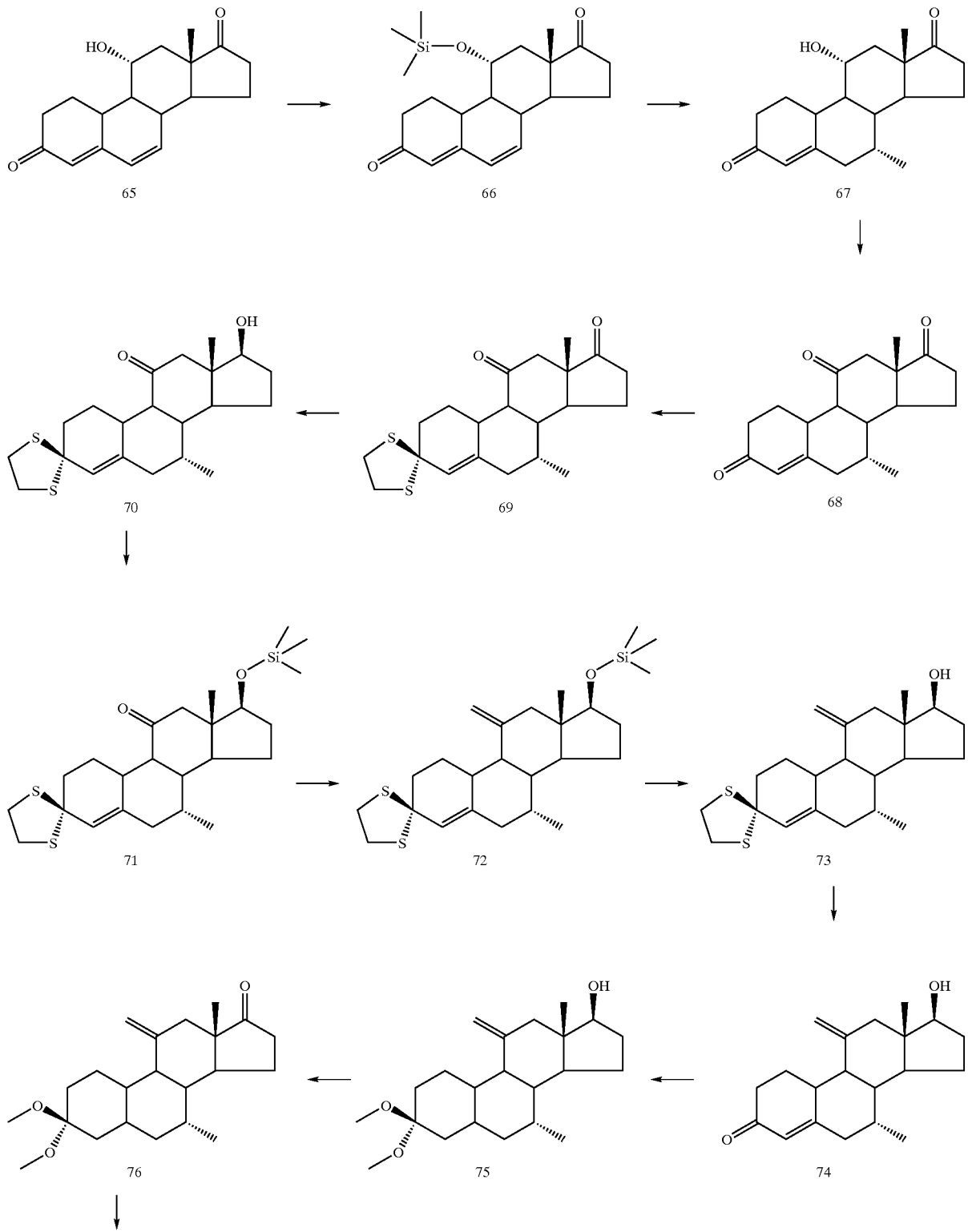
Scheme VII

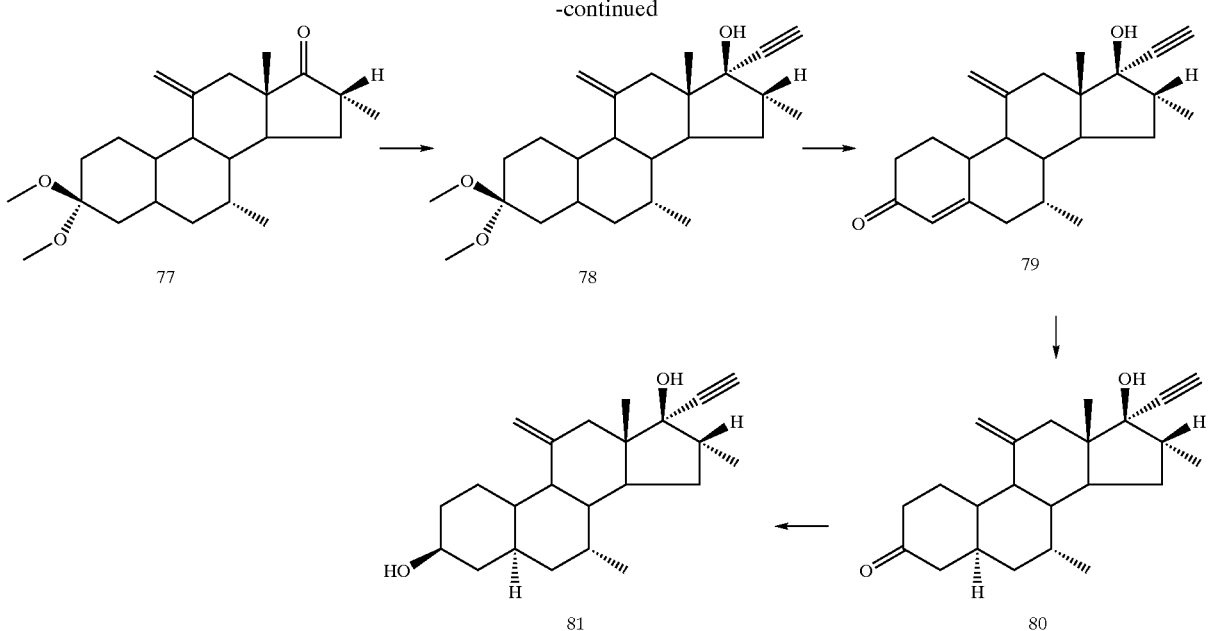

66

To a solution of 10 g of 11α-hydroxynordienedione (65) in 45 ml of DMF was added 10 g of imidazole, followed at 0° C. by 8.6 ml of trimethylsilyl chloride. After stirring for 1 hr the mixture was poured into ice water and the product was extracted with ethyl acetate. The crude material was chromatographed and then triturated with heptane, to provide 7.8 g of 11-trimethylsilyloxy derivative 66, Mp 89–90° C., NMR δ 4.08 (r, 1, 11αH), 5.80 (s, 1H, H4), 6.25 (m, 2, H6,7)., 0.15 (s, 9, trimethylsilyl).

67

To a solution of 5.3 g of 66 and 500 mg of Cu(Oac)$_2$ in 20 ml of THF was added at −30° C. dropwise 9.8 ml of 1M methylmagnesium chloride in THF. The mixture was stirred for 1 h and then poured into a solution of 6 ml of conc. sulphuric acid in 300 ml of water and stirred overnight. The product was extracted with ethyl acetate, dried and concentrated, providing 4.8 g of solid material pure enough for further reaction. NMR δ 5.85 (s, 1, H4), 3.92 (m, 1, H11α), 0.83 (d, 3, 7αCH$_3$), 0.95 (s, 3, 18CH$_3$); R$_f$ 0.22 (hept/ethyl ac. 7/3) starting material R$_f$ 0.65.

68

To a solution of 4.8 g of 67, and 6.6 g of NMO in 100 ml of acetone was added 130 mg of tetrapropylammonium perruthenate. After stirring for 2 h 2 g of silica gel, followed by 100 ml A heptane were added. The mixture was stirred for an additional ½ h and filtered over Celite. The filtrate was concentrated and the residue treated with diisopropyl ether, to provide 4 g of essentially pure trione 68. NMR δ 5.89 (s, 1, H4), 0.89 (s, 3, 18CH$_3$), 0.92 (d, 3, 7αCH$_3$); R$_f$ 0.46 (hept./ethyl ac. 7/3) starting material R$_f$ 0.24.

69

A mixture of 3.5 g of steroid 68, 1.3 ml of ethanedithiol, 300 mg of p-toluenesulfonic acid and 35 ml of ethanol was refluxed for 1 h. The reaction was cooled to room temperature and 80 ml of cold ½ N NaOH was added. After stirring for 1 h the product was filtered and washed with cold water. After drying in vacuo at 50° C. 4.6 g of 69 were obtained; NMR δ 5.66 (s, 1, H4), 3.22 and 3.38 (m, 4, thioketal), 0.85 (s, 3, 18CH$_3$), 0.88 (d, 3, 7αCH$_3$); R$_f$ 0.88 (toluene/ac 7/3) starting mat. R$_f$ 0.59.

70

To a solution of 4.0 g of 69 in a mixture of 100 m of methanol and 50 ml of methylene chloride was added at −20° C. 450 mg of NaBH$_4$ in smaportions. After stirring for an additional 1 h the reduction was complete and the reaction was treated with S ml of acetone and then concentrated to a small volume and diluted with 100 ml of water and extracted with methylene chloride. After drying and concentration 3.9 g of essentially pure 70 was obtained;

NMR δ 3.90 (m, 1, 17αH), 0.82 (d, 3, 7αCH$_3$), 0.73 (s, 3, 18CH$_3$); R$_f$ 0.39 (hept./ethyl 1/1) starting material R$_f$ 0.65.

71

A solution of 2.5 ml of trimethylsilyl chloride in 20 ml of ether was added dropwise to a mixture of 4.7 g of 70 and 2.6 g of imidazole in 50 ml of DMF at 0° C. After stirring for 1 h the reaction was diluted with ice water and the product extracted with ethyl acetate. After drying and concentration of the organic phase the residue was triturated with 80%aq. ethanol at an ice bath and filtered,and dried at 50° C. in vacuo, to provide 5.2 g of 71; NMR δ 3.76 (t, 1, 17αH), 0.65 (s, 3, 18CH$_3$), 0.80 (d, 3, 7αCH$_3$), 5.60 (s, 1, H4); R$_f$ 0.86 (hept./etyl ac. 1/1) starting material R$_f$ 0.37.

73

A suspension of 4.4 g of potassium tert-butoxide and 16.2 g of methyltriphenylphosphoniurm bromide in 130 ml of toluene was heated at 100° C. for ½ hr under nitrogen atmosphere. The yellow mixture was cooled to 50° C. and a solution of 4.6 g of steroid 71 in 20 ml of toluene was added. The reaction was stirred for another 1 h at 100° C., cooled and poured into 500 ml of ice water. The product was extracted with toluene and washed, dried and concentrated. The residue was chromatographed over toluene/silica gel to remove most of the reagent contamination. The crude 72 thus obtained (6.3 g) was dissolved in 20 m of THF and a solution of 18 ml of 1M TBAF in THF was added. After stirring for ½ h the mixture was diluted with water and extracted with ethyl acetate. The product thus obtained was purified by chromatography, providing 4.7 g of 73, Mp 177–180; NMR δ 4.77 and 4.86 (AB, 2, methylene H's) 5.60 (s, 1, H4), 3.72 (m, 1, 17αH)0.70 (s, 3, 18CH$_3$), 0.77 (d, 3, 7α-CH$_3$); R$_f$ 0.10 (hept./ethyl ac. 9/1) starting material R$_f$ 0.73.

74

A solution of 2.45 g of periodic acid in a mixture of 12 ml of water and 12 ml of methanol was added to a solution of 4.7 g of 73 in 40 ml of methylene chloride. The mixture was stirred for 45 min. and then diluted with water. The product was extracted with methylene chloride. The organic layer was washed several times with 5% aq.sodium thiosulphate solution and water and then dried and concentrated. The residue was purified by column chromatography over silica gel to provide 2.6 g of 74; NMR δ 0.73 (s, 3, 18CH$_3$), 0.79 (d, 3, 7αCH$_3$), 5.88 (s, 1, H4), 4.83, 4.94 (AB, 2, methylene H's), 3.78 (m, 1, 17αH); R$_f$ 0.25 (hept./ethyl ac. 6/4) starting mat. R$_f$ 0.48.

75

A mixture of 2.6 g of 74, 7 ml of trinethylorthoformate, 480 mg of p-toluenesulphonic acid and 50 ml of methanol was stirred at room temperature while monitoring the reaction by tlc. After 2.5 h the reaction was poured onto sat. aq. NaHCO$_3$ and extracted with ethyl acetate. After drying and concentration in vacuo 3.1 g of a 1/1 mixture of Δ5,6 and Δ5(10) ketal was obtained; R$_f$ 0.46 (hept./ethyl ac. 6/4) starting material R$_f$ 0.25; NMR(1/1 mixture of ketals) δ 3.15, 3.22, 3.24 (singulets, 6, signals of OCH$_3$), 0.77, 0.87 (2×d, 3, 7αCH$_3$), 0.65, 0.71 (2×s, 3, 18CH$_3$).

76

The crude product 75 was dissolved in 60 ml of acetone. To this were added 3.7 g of N-methylmorpholine-N-oxide and 75 mg of tetrapropylammonium perruthenate. The mixture was stirred for 2 h. then 1 g of silicagel and 60 ml of heptane were added. Upon stirring for 15 min. the reaction was filtered over Celite and the filtrate concentrated to dryness. The residue was pased through a short silica column and provided 1.9 g of the ketone 76 as a mixture of Δ5(10) and Δ5,6 ketals; NMR typical signals at δ 0.82, 0.93 (2×d, 3, 7αCH$_3$), 0.79, 0.85 (2×s, 3, 18CH$_3$), 3.15, 3.22, 3.25 (s, 6, signals of OCH$_3$), 4.70,4.85 and 4.87 and 4.93 (2×AB, 2, methylene H's); R$_f$ 0.58 (hept./ethyl ac. 6/4), starting material R$_f$ 0.45.

77

A solution of 500 mg of 76 in 10 ml of THF and 0.4 ml of DMPU was added dropwise at −40° C. to a solution of 1.6 ml of 1M Li-hexamethyldisilazide in 10 ml of THF. After stirring for an additional 45 min, 120 μl of methyliodide was added. Stirring was continued for 1 h at −20° C. and then the reaction was poured into water and the product extracted with ethyl acetate. The material obtained after washing, drying and concentration of the organic phase was passed through a silica column, and provided 510 mg of 16α-methyl derivative 77, as a mixture of double bond isomers; R$_f$ 0.56 (hept./ethyl ac. 7/3) starting material R$_f$ 0.48. NMR δ 1.15, 1.17 (2×d, 16αCH$_3$).

78

Li-acetylide was generated by dropwise addition of 7.1 ml of 1.6M BuLi-hexane to 0.46 ml of 1,2-dibromoethene in 10 ml of THF at −60° C. After stirring for ½ h a solution of 500 mg of steroid 77 in 10 ml of THF was added and the reaction mixture was stirred for ½ h while allowing the temperature rise to room temperature during this period. Water was then added and the product extracted with ethyl acetate. The material thus obtained was passed through a short silica column, and provided 540 mg of 78 as double bond isomer mixture.NMR δ 2.74 and 2.76 (2×s, 1, acetylene), 1.17, 1.19 (2×d, 3, 16αCH$_3$), 0.78, 0.88 (2×d, 3, 7αCH$_3$); R$_f$ 0.50 (hept./ethyl ac. 7/3), starting material R$_f$ 0.60.

79

To a solution of 440 mg of 78 in 20 ml of acetone was added 4 ml of 4N HCl. After stirring for the 1 h the reaction was complete, and the mixture was poured into sat. aq. NaHCO3 and extracted with ethyl acetate. Upon washing, drying and concentrating, 380 mg of essentially pure 79 were obtained, directly used in the next step; NMR δ 5.88 (s, 1, H-4), 5.90 (AB, 2, methylene), 2.76 (s, 1, acetylene), 1.18 (d, 3, 16αCH$_3$), 0.88 (s, 3, 18-CH$_3$), 0.79 (d, 3, 7αCH$_3$).

80

To a solution of 280 mg of 79 in a mixture of 30 ml of liq.NH$_3$ and and 10 ml of THF at −40° C. were added small pieces of Li foil until the blue color persisted for 15 min. Then the small excess of Li was quickly quenched by addition of solid NH$_4$Cl and ammonia was allowed to evaporate. To the residual material was added 100 ml of water and the mixture was extracted with ethyl acetate. The organic material isolated after washing, drying and concentration contained almost pure 80; R$_f$ 0.57 (hept./ethyl ac. 6/4), NMR δ 4.78. 4.88 (AB, 2, methylene), 2.66 (s, 1, acetylene), 1.19 (d, 3, 16αCH$_3$), 0.86 (s, 3, 18CH$_3$), 0.90 (d, 3, 7αCH$_3$).

81

To a solution of 160 mg of 80 in 10 ml of THF were added at 0° C. small portions of LiAlH$_4$ until the reduction was completed. Then 0.1 ml of sat. aq. Na$_2$SO$_4$ was added followed by some solid Na$_2$SO$_4$ The mixture was stirred for 15 min and then filtered over Celite. The filtrate was concentrated and the residue purified by passing through a preparative HPLC column, packed with reversed phase C-18 silica, using acetonitrile-water as eluent, to provide 55 mg of 81, Mp 198–199° C.; R$_f$ 0.33 (hept./ethyl ac. 6/4) starting material 0.57. NMR δ 3.67 (m, 1, 3αH), 4.70, 4.82 (AB, 2, methylene) 2.65 (s, 1, acetylene),), 1.18 d, 3, 16αCH$_3$), 0.83 (s, 3, 18CH$_3$), 0.89 (d, 3, 7αCH$_3$).

EXAMPLE 8

Compounds are tested for their estrogen receptor activity in a binding assay and in a transactivation assay.

Determination of competitive binding to cytoplasmic human estrogen receptor from rec.CHO cells is used to estimate the relative affinity (potency ratio) of a test compound for estrogen receptors present in the cytosol of recombinant Chinese hamster ovary (CHO) cells, stably transfected with the human estrogen receptor, as compared with estradiol (E$_2$). Cytosol prepared from recombinant CHO cells, stably transfected with the human estrogen receptor. The cell line has been made within the Department of Biotechnology and Biochemistry (BBC) (N.V. Organon) and is known under the name CHO-ER (2B1). Reference compounds are ethinylestradiol and estriol.

The antiestrogenic activity of compounds is determined in an in vitro bioassay with recombinant Chinese hamster ovary (CHO) cells stably co-transfected with the human estrogen receptor α (hERα) or β receptor (hERβ), the rat oxytocin promoter (RO) and the luciferase reporter gene (LUC). The antiestrogenic activity (potency ratio) of a test compound to inhibit the transactivation of the enzyme luciferase mediated via the estrogen receptor by the estrogen Org 2317 (estradiol, 1, 3, 5 (10)-estratriene-3,17β-diol) is compared with the standard Org 34790 (ICI 164.384; (7α, 17β)-N-butyl-3,17-dihydroxy-N-methylestra-1,3,5 (10)-triene-7-undecanamide).

Test medium: Intact recombinant CHO cells stably co-transfected with the human estrogen receptor, the rat oxytocin promoter and the luciferase reporter gene. The cell line has been produced within the Department of Biotechnology and Biochemistry (BBC) (N.V. Organon) and is known under the name CHO-ERRO 2B1-1E9.

The results are presented in the Table below.

The data are expressed in percentage of the action of the reference compound in the assay

TABLE

| Compound | α-binding. | α-transactivation | β-binding | β-transactivation |
|---|---|---|---|---|
| 11 | 57 | 58 | 1.1 | 0.8 |
| 15 | 35 | 27 | 0.3 | 0.3 |
| 21 | 8.6 | 7.7 | 0.2 | 0.1 |
| 31 | 37 | 9.6 | 0.1 | 0.2 |
| 32 | 2,6 | 2.4 | <0.1 | 0.1 |
| 42 | 29 | 2 | 0.1 | <0.04 |
| 43 | 11.9 | 1.3 | 0.1 | <0.1 |
| 54 | 27,5 | 29.7 | 0.1 | 1.0 |
| 55 | 36 | 61.5 | 0.1 | 1.9 |
| 63 | 25 | 22 | 0.4 | 0.1 |
| 64 | 35 | 29 | 0.2 | 0.2 |
| 81 | n.t.r. | 27 | n.t.r. | 0.1 | n.t.r.: No test results available

What is claimed is:

1. A non-aromatic steroid represented by formula I,

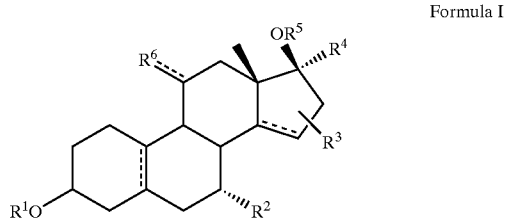

Formula I wherein, $R^1$ is H, $(C_1-C_3)$alkyl or $(C_2-C_3)$acyl;

$R^2$ as H, α-$(C_1-C_4)$alkyl, α-$(C_2-C_4)$alkenyl or α-$(C_2-C_4)$alkynyl;

$R^3$ is H, $(C_1-C_4)$alkyl, $(C_2-C_4)$alkenyl or $(C_2-C_4)$alkynyl, each at location 15 or 16 of the steroid skeleton;

$R^4$ is H, $(C_1-C_5)$alkyl, $(C_2-C_5)$alkenyl or $(C_2-C_5)$alkynyl, each may be unsubstituted or substituted with halogen atom;

$R^5$ is H, $(C_1-C_3)$alkyl or $(C_2-C_3)$acyl;

$R^6$ is $(C_1-C_5)$alkyl, $(C_2-C_5)$alkenyl, $(C_2-C_5)$alkynyl or $(C_1-C_5)$alkylidene, each may be unsubstituted or substituted with halogen or $(C_1-C_3)$alkoxy; and dotted lines represented optional double bonds.

2. The non-aromatic steroid according to claim 1, represented by formula II,

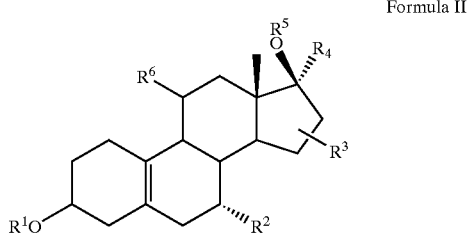

Formula II wherein, $R^1$ is H, $(C_1-C_3)$alkyl or $(C_2-C_3)$acyl;

$R^2$ is H, α-$(C_1-C_4)$alkyl, α-$(C_2-C_4)$alkenyl or α-$(C_2-C_4)$alkynyl;

$R^3$ is H, $(C_1-C_4)$alkyl at location 16 of the steroid skeleton;

$R^4$ is ethynyl $R^5$ is H, $(C_1-C_3)$alkyl, or $(C_2-C_3)$acyl; and $R^6$ is $(C_1-C_5)$alkyl, $(C_2-C_5)$alkenyl, or $(C_2-C_5)$alkynyl, each may be unsubstituted or substituted with chlorine or fluorine.

3. The non-aromatic estrogenic steroid according to claim 2, wherein $R^1$ is H;

$R^2$ is H;

$R^3$ is H, α-methyl at position 16 or α-ethyl at position 16;

$R^4$ is ethynyl;

$R^5$ is H; and $R^6$ is propenyl, allyl or butenyl.

4. A pharmaceutical composition, comprising:

a steroid compound according to claim 1, and pharmaceutically acceptable auxiliaries.

5. The non-aromatic estrogenic steroid according to claim 1, wherein $R^4$ is ethynyl.

6. The pharmaceutical composition according claim 4, wherein the steroid compounds is reoresented by formula II

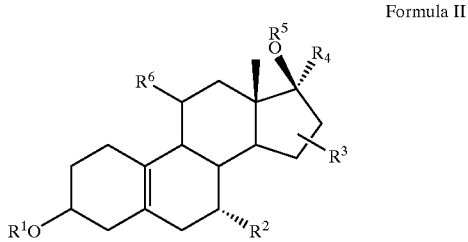

Formula II wherein, $R^1$ is H, $(C_1-C_3)$alkyl or $(C_2-C_3)$acyl;

$R^2$ is H, α-$(C_1-C_4)$alkyl, α-$(C_2-C_4)$alkenyl or α-$(C_2-C_4)$alkynyl;

$R^3$ is H, $(C_1-C_4)$alkyl at location 16 of the steroid skeleton;

$R^4$ is ethynyl $R^5$ is H, $(C_1-C_3)$alkyl, or $(C_2-C_3)$acyl; and $R^6$ is $(C_1-C_5)$alkyl, $(C_2-C_5)$alkenyl, or $(C_2-C_5)$alkynyl, each may be unsubstituted or substituted with chlorine or fluorine.

7. A method for treating an estrogen-deficiency dependent disorder in a patient suffering from such a disorder, comprising:

administering an effective amount to a patient in need thereof a non-aromatic estrogenic steroid compound represented by formula I Formula I

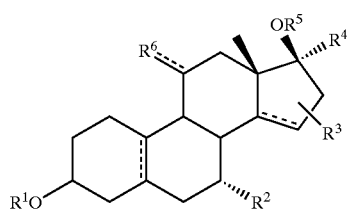

wherein,
$R^1$ is H, $(C_1-C_3)$alkyl or $(C_2-C_3)$acyl;
$R^2$ is H, $\alpha$-$(C_1-C_4)$alkyl, $\alpha$-$(C_2-C_4)$alkenyl or $\alpha$-$(C_2-C_4)$alkynyl;
$R^3$ is H, $(C_1-C_4)$alkyl, $(C_2-C_4)$alkenyl or $(C_2-C_4)$alkynyl, each at location 15 or 16 of the steroid skeleton;
$R^4$ is H, $(C_1-C_5)$alkyl, $(C_2-C_5)$alkenyl or $(C_2-C_5)$alkynyl, each may be unsubstituted or substituted with halogen atom;
$R^5$ is H, $(C_1-C_3)$alkyl or $(C_2-C_3)$acyl;
$R^6$ is $(C_1-C_5)$alkyl, $(C_2-C_5)$alkenyl, $(C_2-C_5)$alkynyl or $(C_1-C_5)$alkylidene, each may be unsubstituted or substituted with halogen or $(C_1-C_3)$alkoxy; and
dotted lines represent optional double bonds.

8. The method according to claim 7, wherein the steroid compound is represented by formula II Formula II

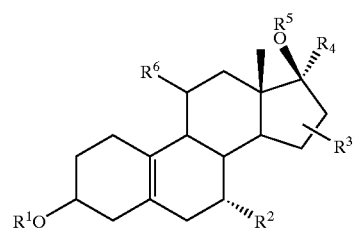

wherein,
$R^1$ is H, $(C_1-C_3)$alkyl or $(C_2-C_3)$acyl;
$R^2$ is H, $\alpha$-$(C_1-C_4)$alkyl, $\alpha$-$(C_2-C_4)$alkenyl or $\alpha$-$(C_2-C_4)$alkynyl;
$R^3$ is H, $(C_1-C_4)$alkyl at location 16 of the steroid skeleton;
$R^4$ is ethynyl
$R^5$ is H, $(C_1-C_3)$alkyl, or $(C_2-C_3)$acyl; and
$R^1$ is $(C_1-C_5)$alkyl, $(C_2-C_5)$alkenyl or $(C_2-C_5)$alkynyl, each may be unsubstituted or substituted with chlorine or fluorine.

9. The method according to claim 7, wherein $R^4$ is ethynyl.

* * * * *